(12) United States Patent  
Carrillo, Jr.

(10) Patent No.: US 8,647,256 B2
(45) Date of Patent: Feb. 11, 2014

(54) GUIDEWIRE LOCKING DEVICE AND METHOD

(75) Inventor: Oscar Carrillo, Jr., Attleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 341 days.

(21) Appl. No.: 12/891,066

(22) Filed: Sep. 27, 2010

(65) Prior Publication Data

US 2011/0015482 A1   Jan. 20, 2011

Related U.S. Application Data

(63) Continuation of application No. 11/074,981, filed on Mar. 8, 2005, now Pat. No. 7,803,107, which is a continuation of application No. 10/370,173, filed on Feb. 19, 2003, now Pat. No. 6,893,393.

(51) Int. Cl.
 *A61B 1/00* (2006.01)
 *A61M 5/178* (2006.01)

(52) U.S. Cl.
 USPC ....... 600/104; 600/102; 600/154; 604/164.13

(58) Field of Classification Search
 USPC .............................. 600/104, 154; 604/164.13
 See application file for complete search history.

(56) References Cited

U.S. PATENT DOCUMENTS

| | | | |
|---|---|---|---|
| 1,204,053 A | 11/1916 | Moore | |
| 2,623,520 A | 12/1952 | Bamford, Jr. et al. | |
| 3,015,869 A | 1/1962 | Rapata | |
| 3,536,281 A | 10/1970 | Meehan et al. | |
| 3,677,243 A | 7/1972 | Nerz | |
| 4,306,562 A | 12/1981 | Osborne | |
| 4,345,606 A | 8/1982 | Littleford | |
| 4,411,654 A | 10/1983 | Boarini et al. | |
| 4,412,832 A | 11/1983 | Kling et al. | |
| 4,453,933 A | * 6/1984 | Speaker .................. | 604/179 |
| 4,474,174 A | 10/1984 | Petruzzi | |
| RE31,855 E | 3/1985 | Osborne | |

(Continued)

FOREIGN PATENT DOCUMENTS

DE 4115007 A1 11/1992
EP 0328760 A2 8/1989

(Continued)

OTHER PUBLICATIONS

Arndorfer Inc. Information Sheet, dated on or before Mar. 6, 2000, 7 sheets.

(Continued)

*Primary Examiner* — Alireza Nia
(74) *Attorney, Agent, or Firm* — Seager, Tufte & Wickhem LLC

(57) ABSTRACT

A locking device for a maintaining an elongated member at a selected place within a body lumen includes a substantially rigid body including an attachment portion adapted to be coupled to a proximal portion of a medical instrument. When in an operative position, the distal portion of the medical instrument is received within the body lumen and a head coupled to the substantially rigid body. The head is configured to overlie an access port of the medical device when the attachment portion is coupled to the proximal portion of the medical device in a predetermined configuration. A plurality of locking features extends from the head to immobilize a section of the elongated member relative to the medical device.

11 Claims, 10 Drawing Sheets

(56) References Cited

U.S. PATENT DOCUMENTS

| | | |
|---|---|---|
| 4,509,944 A | 4/1985 | King et al. |
| 4,687,470 A | 8/1987 | Okada |
| 4,696,668 A | 9/1987 | Wilcox |
| 4,700,694 A | 10/1987 | Shishido |
| 4,715,360 A | 12/1987 | Akui et al. |
| 4,723,942 A | 2/1988 | Scott |
| 4,748,982 A | 6/1988 | Horzewski et al. |
| 4,762,129 A | 8/1988 | Bonzel |
| 4,771,777 A | 9/1988 | Horzewski et al. |
| 4,781,677 A | 11/1988 | Wilcox |
| 4,835,824 A | 6/1989 | Durham et al. |
| 4,844,092 A | 7/1989 | Rydell et al. |
| 4,900,184 A | 2/1990 | Cleveland |
| 4,905,667 A | 3/1990 | Foerster et al. |
| 4,917,103 A | 4/1990 | Gambale et al. |
| 4,927,418 A | 5/1990 | Dake et al. |
| 4,928,669 A | 5/1990 | Sullivan |
| 4,928,693 A | 5/1990 | Goodin et al. |
| 4,932,413 A | 6/1990 | Shockey et al. |
| 4,946,443 A | 8/1990 | Hauser et al. |
| 4,973,329 A | 11/1990 | Park et al. |
| 4,983,168 A | 1/1991 | Moorehead |
| 4,988,356 A | 1/1991 | Crittenden et al. |
| 4,995,872 A | 2/1991 | Ferrara |
| 4,997,421 A | 3/1991 | Palsrok et al. |
| 5,040,548 A | 8/1991 | Yock |
| 5,061,273 A | 10/1991 | Yock |
| 5,064,414 A | 11/1991 | Revane |
| 5,125,915 A | 6/1992 | Berry et al. |
| 5,135,535 A | 8/1992 | Kramer |
| 5,139,032 A | 8/1992 | Jahrmarkt et al. |
| 5,147,377 A | 9/1992 | Sahota |
| 5,158,545 A | 10/1992 | Trudell et al. |
| 5,161,534 A | 11/1992 | Berthiaume |
| 5,167,634 A | 12/1992 | Corrigan, Jr. et al. |
| 5,180,367 A | 1/1993 | Kontos et al. |
| 5,191,888 A | 3/1993 | Palmer et al. |
| 5,195,978 A | 3/1993 | Schiffer |
| 5,205,822 A | 4/1993 | Johnson et al. |
| 5,219,335 A | 6/1993 | Willard et al. |
| 5,232,445 A | 8/1993 | Bonzel |
| 5,248,306 A | 9/1993 | Clark et al. |
| 5,250,033 A | 10/1993 | Evans et al. |
| 5,263,932 A | 11/1993 | Jang |
| 5,267,958 A | 12/1993 | Buchbinder et al. |
| 5,279,562 A | 1/1994 | Sirhan et al. |
| 5,281,203 A | 1/1994 | Ressemann |
| 5,282,479 A | 2/1994 | Havran |
| 5,290,232 A | 3/1994 | Johnson et al. |
| 5,290,241 A | 3/1994 | Kraus et al. |
| 5,300,085 A | 4/1994 | Yock |
| 5,306,247 A | 4/1994 | Pfenninger |
| 5,308,318 A | 5/1994 | Plassche, Jr. |
| 5,314,408 A | 5/1994 | Salmon et al. |
| 5,320,602 A | 6/1994 | Karpiel |
| 5,324,259 A | 6/1994 | Taylor et al. |
| 5,324,269 A | 6/1994 | Miraki |
| 5,328,472 A | 7/1994 | Steinke et al. |
| 5,334,143 A | 8/1994 | Carroll |
| 5,334,147 A | 8/1994 | Johnson |
| 5,334,187 A | 8/1994 | Fischell et al. |
| 5,336,184 A | 8/1994 | Teirstein |
| 5,342,297 A | 8/1994 | Jang |
| 5,350,395 A | 9/1994 | Yock |
| 5,357,978 A | 10/1994 | Turk |
| 5,364,355 A | 11/1994 | Alden et al. |
| 5,364,376 A | 11/1994 | Horzewski et al. |
| 5,368,567 A | 11/1994 | Lee |
| 5,370,623 A | 12/1994 | Kreamer |
| 5,380,283 A | 1/1995 | Johnson |
| 5,387,226 A | 2/1995 | Miraki |
| 5,389,087 A | 2/1995 | Miraki |
| 5,395,335 A | 3/1995 | Jang |
| 5,397,302 A | 3/1995 | Weaver et al. |
| 5,409,459 A | 4/1995 | Gambale |
| 5,413,559 A | 5/1995 | Sirhan et al. |
| 5,415,639 A | 5/1995 | VandenEinde et al. |
| 5,448,993 A | 9/1995 | Lynch et al. |
| 5,449,363 A | 9/1995 | Brust et al. |
| 5,451,233 A | 9/1995 | Yock |
| 5,454,790 A | 10/1995 | Dubrul |
| 5,458,584 A | 10/1995 | Ginn et al. |
| 5,458,605 A | 10/1995 | Klemm |
| 5,462,530 A | 10/1995 | Jang |
| 5,480,389 A | 1/1996 | McWha et al. |
| 5,489,271 A | 2/1996 | Andersen |
| 5,490,837 A | 2/1996 | Blaeser et al. |
| 5,496,346 A | 3/1996 | Horzewski et al. |
| 5,501,227 A | 3/1996 | Yock |
| 5,531,700 A | 7/1996 | Moore et al. |
| 5,536,248 A | 7/1996 | Weaver et al. |
| 5,540,236 A | 7/1996 | Ginn |
| 5,599,299 A | 2/1997 | Weaver et al. |
| 5,599,300 A | 2/1997 | Weaver et al. |
| 5,613,949 A | 3/1997 | Miraki |
| 5,626,600 A | 5/1997 | Horzewski et al. |
| 5,634,475 A | 6/1997 | Wolvek |
| 5,685,853 A | 11/1997 | Bonnet |
| 5,693,015 A | 12/1997 | Walker et al. |
| 5,706,827 A | 1/1998 | Ehr et al. |
| 5,718,680 A | 2/1998 | Kraus et al. |
| 5,725,504 A | 3/1998 | Collins |
| 5,765,682 A | 6/1998 | Bley |
| 5,788,681 A | 8/1998 | Weaver et al. |
| 5,800,414 A | 9/1998 | Cazal |
| 5,833,706 A | 11/1998 | St. Germain et al. |
| 5,843,028 A | 12/1998 | Weaver et al. |
| 5,849,016 A | 12/1998 | Suhr |
| 5,851,189 A | 12/1998 | Forber |
| 5,921,971 A | 7/1999 | Agro et al. |
| 5,935,114 A | 8/1999 | Jang et al. |
| 5,978,699 A | 11/1999 | Fehse et al. |
| 6,007,522 A | 12/1999 | Agro et al. |
| 6,096,009 A * | 8/2000 | Windheuser et al. .... 604/165.01 |
| 6,106,487 A | 8/2000 | Duane et al. |
| 6,117,070 A | 9/2000 | Akiba |
| 6,152,910 A | 11/2000 | Agro et al. |
| 6,190,333 B1 | 2/2001 | Valencia |
| 6,190,358 B1 | 2/2001 | Fitzmaurice et al. |
| 6,200,262 B1 | 3/2001 | Ouchi |
| 6,277,100 B1 | 8/2001 | Raulerson et al. |
| 6,312,404 B1 | 11/2001 | Agro et al. |
| 6,322,577 B1 | 11/2001 | McInnes |
| 6,346,093 B1 | 2/2002 | Allman et al. |
| 6,517,518 B2 | 2/2003 | Nash et al. |
| 6,520,951 B1 | 2/2003 | Carrillo, Jr. et al. |
| 6,582,401 B1 | 6/2003 | Windheuser et al. |
| 6,606,515 B1 | 8/2003 | Windheuser et al. |
| 6,663,597 B1 | 12/2003 | Windheuser et al. |
| 6,679,872 B2 | 1/2004 | Turovskiy et al. |
| 6,746,442 B2 | 6/2004 | Agro et al. |
| 6,746,466 B2 | 6/2004 | Eidenschink et al. |
| 6,827,683 B2 * | 12/2004 | Otawara ................. 600/123 |
| 6,869,416 B2 | 3/2005 | Windheuser et al. |
| 6,893,393 B2 | 5/2005 | Carrillo |
| 2001/0029362 A1 | 10/2001 | Sirhan et al. |
| 2002/0007152 A1 | 1/2002 | Hermann et al. |
| 2002/0016612 A1 | 2/2002 | Ashby et al. |
| 2003/0088153 A1 | 5/2003 | Carrillo, Jr. et al. |
| 2003/0233043 A1 | 12/2003 | Windheuser et al. |
| 2004/0106852 A1 | 6/2004 | Windheuser et al. |
| 2004/0193142 A1 | 9/2004 | Agro et al. |
| 2005/0090835 A1 | 4/2005 | Deal et al. |
| 2006/0195117 A1 | 8/2006 | Rucker et al. |

FOREIGN PATENT DOCUMENTS

| | | |
|---|---|---|
| EP | 0388112 A2 | 9/1990 |
| EP | 0792657 A2 | 9/1997 |
| EP | 0801955 B1 | 3/1999 |
| JP | 50108287 U | 9/1975 |
| JP | 7155382 A | 6/1995 |

(56) References Cited

FOREIGN PATENT DOCUMENTS

| WO | 9203963 | 3/1992 |
|----|---------|--------|
| WO | 9633764 | 10/1996 |
| WO | 9810820 | 3/1998 |
| WO | 9810821 | 3/1998 |
| WO | 9938557 | 8/1999 |
| WO | 9959664 | 11/1999 |
| WO | 0069499 | 11/2000 |
| WO | 0069500 | 11/2000 |

OTHER PUBLICATIONS

Knecht, Gregory L., M.D. et al., Double-Channel Fistulotome for Endoscopic Drainage of Pancreatic Pseudocyst,: Gastrointestinal Endoscopy, vol. 37, No. 3, May/Jun. 1991, pp. 356-357.

Seigel, Jerome H., M.D. et al., "Two New Methods for Selective Bile Duct Cannulation and Sphinterotomy," Gastrointestinal Endoscopy, vol. 33, No. 6, Dec. 1987, pp. 438-440.

* cited by examiner

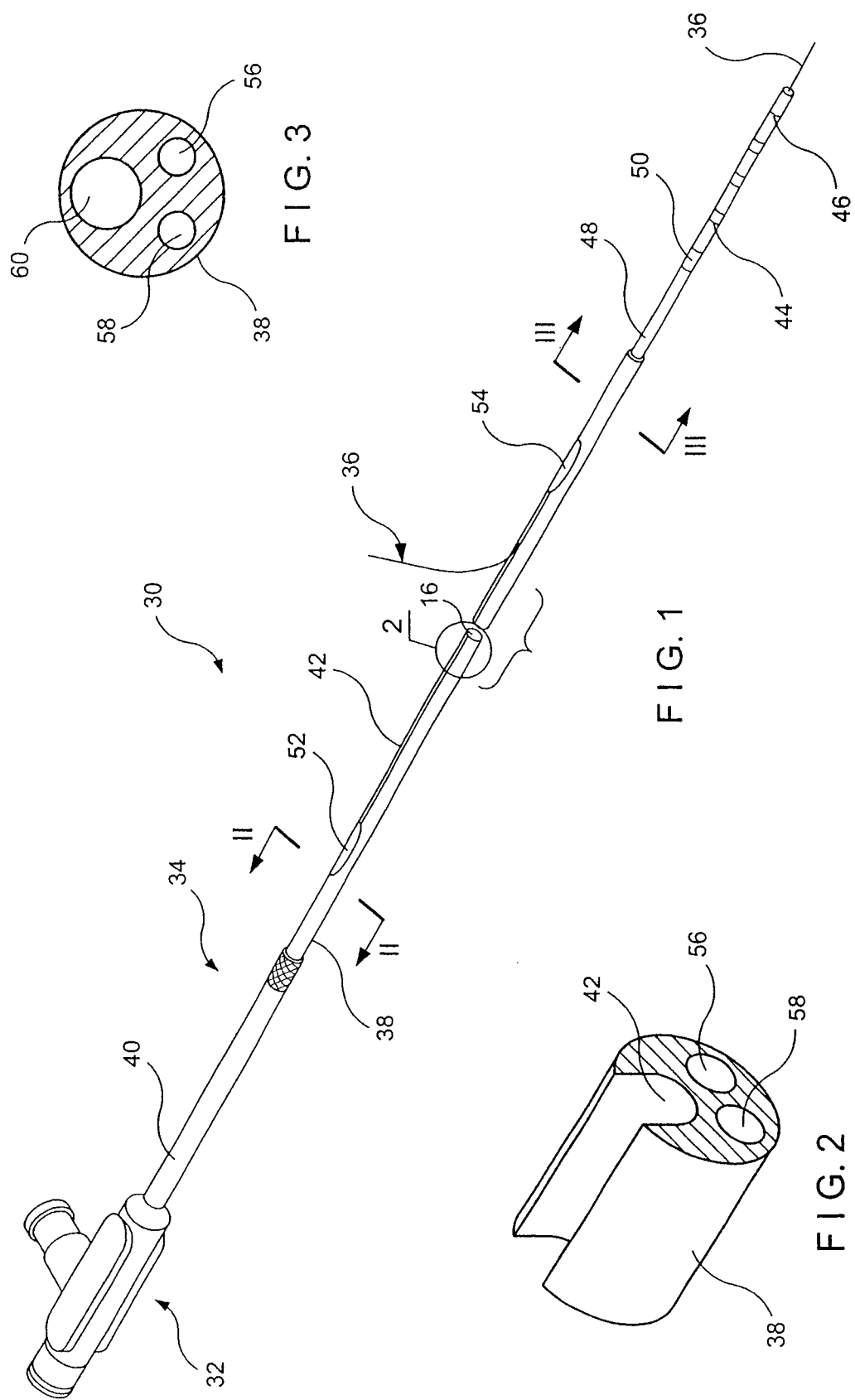

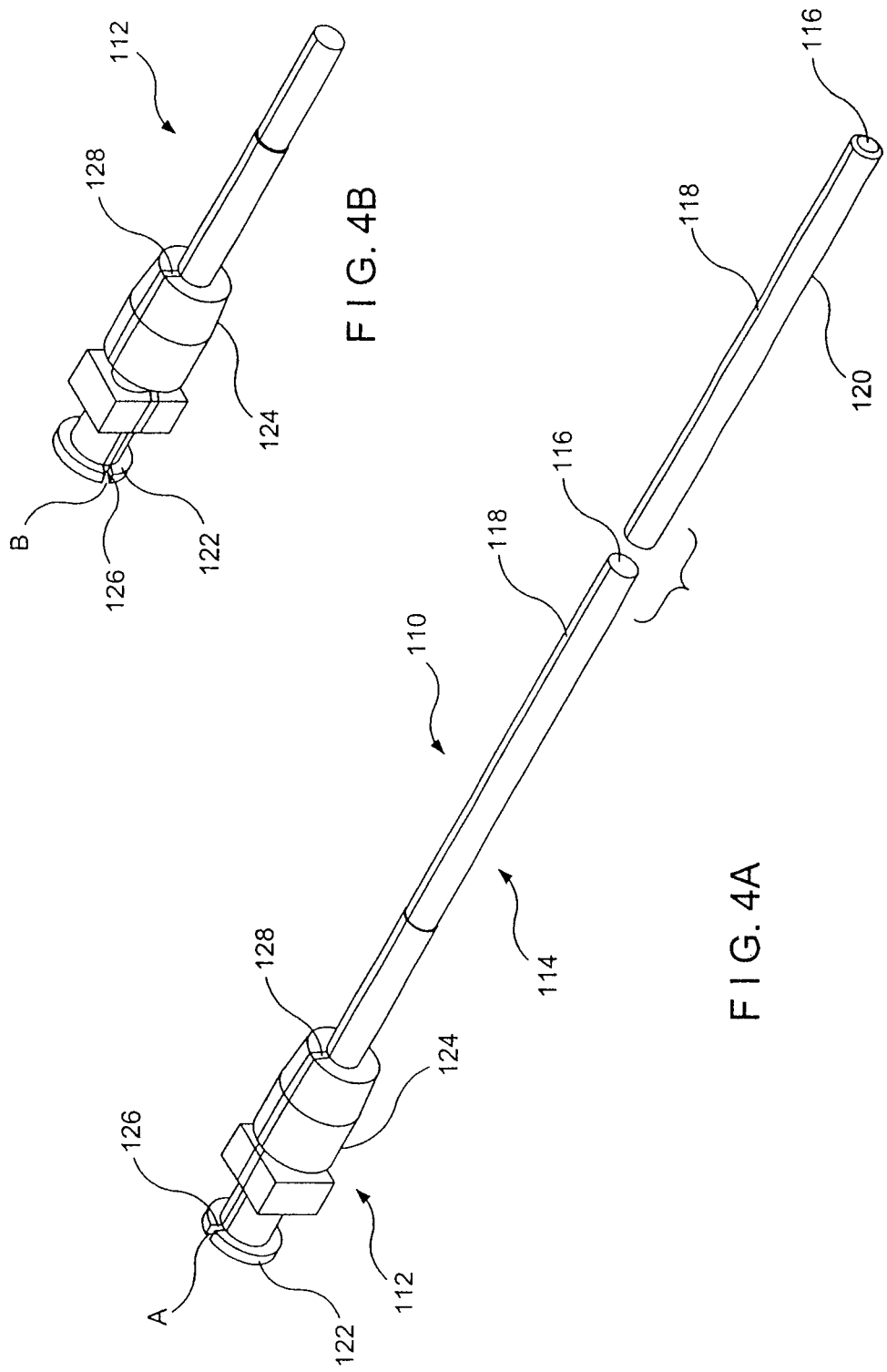

GUIDEWIRE LOCKING DEVICE AND METHOD

CROSS REFERENCE OF CO-PENDING APPLICATION

This application is a continuation of co-pending U.S. application Ser. No. 11/074,981, filed Mar. 8, 2005, which is a continuation of U.S. application Ser. No. 10/370,173, filed Feb. 19, 2003, now U.S. Pat. No. 6,893,393, the entire disclosures of which are incorporated herein by reference.

BACKGROUND

Endoscopic procedures to treat abnormal pathologies of the alimentary canal and the biliary tree are becoming increasingly common. Endoscopes are often used in these procedures to facilitate access to biliary, hepatic and pancreatic ducts, in addition to the larger alimentary passages. The endoscope itself can only provide access to the general area adjacent to the smaller ducts and navigation of the ducts themselves must be carried out using smaller devices, such as catheters and guidewires in conjunction with fluoroscopy. Targeted delivery of therapeutic agents and surgical procedures within the ducts is typically carried out using catheters.

Methods and devices for using catheters to access the biliary tree are described in U.S. Pat. No. 5,397,302 to Weaver et al., and in U.S. Pat. No. 5,320,602 to Karpiel, the disclosures of which are herein incorporated by reference in their entirety. In a general process, treatment of a patient's biliary tree involves introducing an endoscope in the mouth of a patient, and guiding the distal end of the endoscope through the alimentary tract until a distal opening of the endoscope is adjacent to a targeted area to be treated. Additional devices such as catheters may be introduced through the endoscope to the target area, to perform whatever procedure is required to treat the abnormal pathology. In one procedure, a distal end of the catheter is guided through the orifice of the papilla of vater, which leads into the common bile duct and the pancreatic duct. The catheter is inserted through a lumen of the endoscope, so that it emerges in the ducts at the distal end of the endoscope.

A guidewire may be used in conjunction with the catheter to facilitate accessing the desired location. The guidewire is inserted in an opening at the proximal end of the catheter, and is guided through the catheter until it emerges from the catheter's distal end. The guidewire is then pushed to the target in the common bile duct, and the catheter is advanced over the guidewire until the catheter's distal end reaches the desired target position. A catheter may be selected to deliver contrast media to the target area, for fluoroscopic visualization of anatomical detail within the duct. Different catheters specialized for different functions may be necessary to treat the target area that has been visualized, and a catheter exchange may need to be performed. An exchange involves removing the first catheter and replacing it with a second catheter, without displacing the guidewire during the procedure. If the guidewire is displaced, the guidewire must be redirected through the body to the target area, in a difficult and time consuming procedure.

In a conventional procedure, the physician must grasp the proximal end of the guidewire with one hand to immobilize it, and must perform the catheter exchange with the other hand. This procedure is difficult and often results in displacing the guidewire. In addition, it is often necessary to hold in place more than one guidewire at the same time. Manually holding multiple guidewires is extremely difficult when conventional methods and devices are used, since the surgeon has to manually hold the guidewires in place while at the same time replacing one or more catheters. Additional personnel are often required to carry out the procedure using conventional methods.

SUMMARY

The present disclosure is directed to a locking device for maintaining an elongated member at a selected place within a body lumen. The locking device includes a substantially rigid body with an attachment portion adapted to be coupled to a proximal portion of a medical instrument. When in an operative position, the distal portion of the medical instrument is received within the body lumen. A head is coupled to the substantially rigid body. The head is configured to overlie an access port of the medical device when the attachment portion is coupled to the proximal portion of the medical device in a predetermined configuration. A plurality of locking features extends from the head to immobilize a section of the elongated member relative to the medical device. In some embodiments, a locking arm extends from the locking device so that, when the attachment portion is coupled to the medical device, the locking arm extends between the access port and the locking features to guide the elongated member from the access port to the locking features along a desired path.

The present disclosure is further directed to a locking device for maintaining a position within a body lumen of a first elongate member relative to a flexible endoscope while a second elongate member is withdrawn from the body lumen. The locking device includes a mounting mechanism for selectively coupling the locking device to a proximal end of the endoscope. The locking device also includes a head which, when the mounting mechanism is coupled to the endoscope in a predetermined configuration, overlies an opening at a proximal end of the endoscope to a working channel of the endoscope. A plurality of locking features extends from the head to immobilize a portion of the first elongate member relative to the endoscope. In some embodiments, a locking arm extends from the head between the opening at the proximal end of the endoscope and the locking features to limit movement of a portion of the first elongate member between the opening and the locking features.

The present disclosure is further directed to a method of performing a medical procedure. The steps includes inserting an endoscope into a body lumen and inserting a distal end of a first elongate member into the lumen via the access port so that a proximal portion of the first elongate member extends proximally from the access port in combination and immobilizing a portion of the first elongate member relative to the endoscope by engaging a first locking feature of the locking device with the first elongate member. In some embodiments, the method further includes engaging a locking arm of the locking device with the first elongate member to direct the first elongated medical member along a first predetermined path from the proximal end of the endoscope to the first locking feature.

BRIEF DESCRIPTION OF DRAWINGS

FIG. 1 is a perspective view of a catheter according to an embodiment of the present disclosure, having a partially open guidewire lumen;

FIG. 2 is a fragmentary perspective view of the catheter shown in FIG. 1, showing a cross section along plane II;

FIG. 3 is a cross-sectional view of the catheter shown in FIG. 1, taken along line FIGS. 4A and 4B are perspective views showing an endoscope sheath assembly according to an embodiment of the present disclosure;

DETAILED DESCRIPTION

Figure 5:
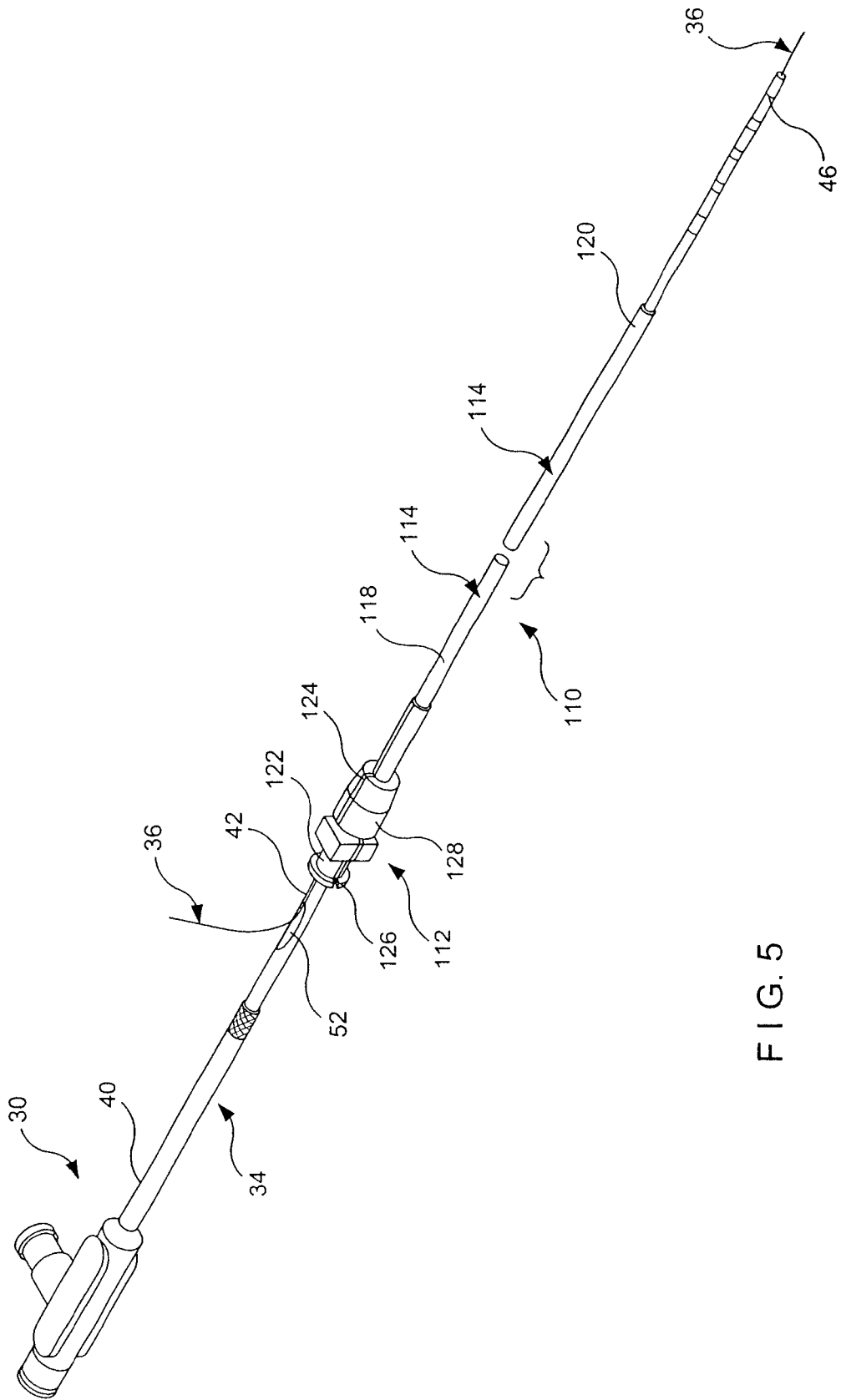
FIG. 5 is a perspective view showing a catheter connected to an endoscope sheath assembly according to the present disclosure.
Figure 6:
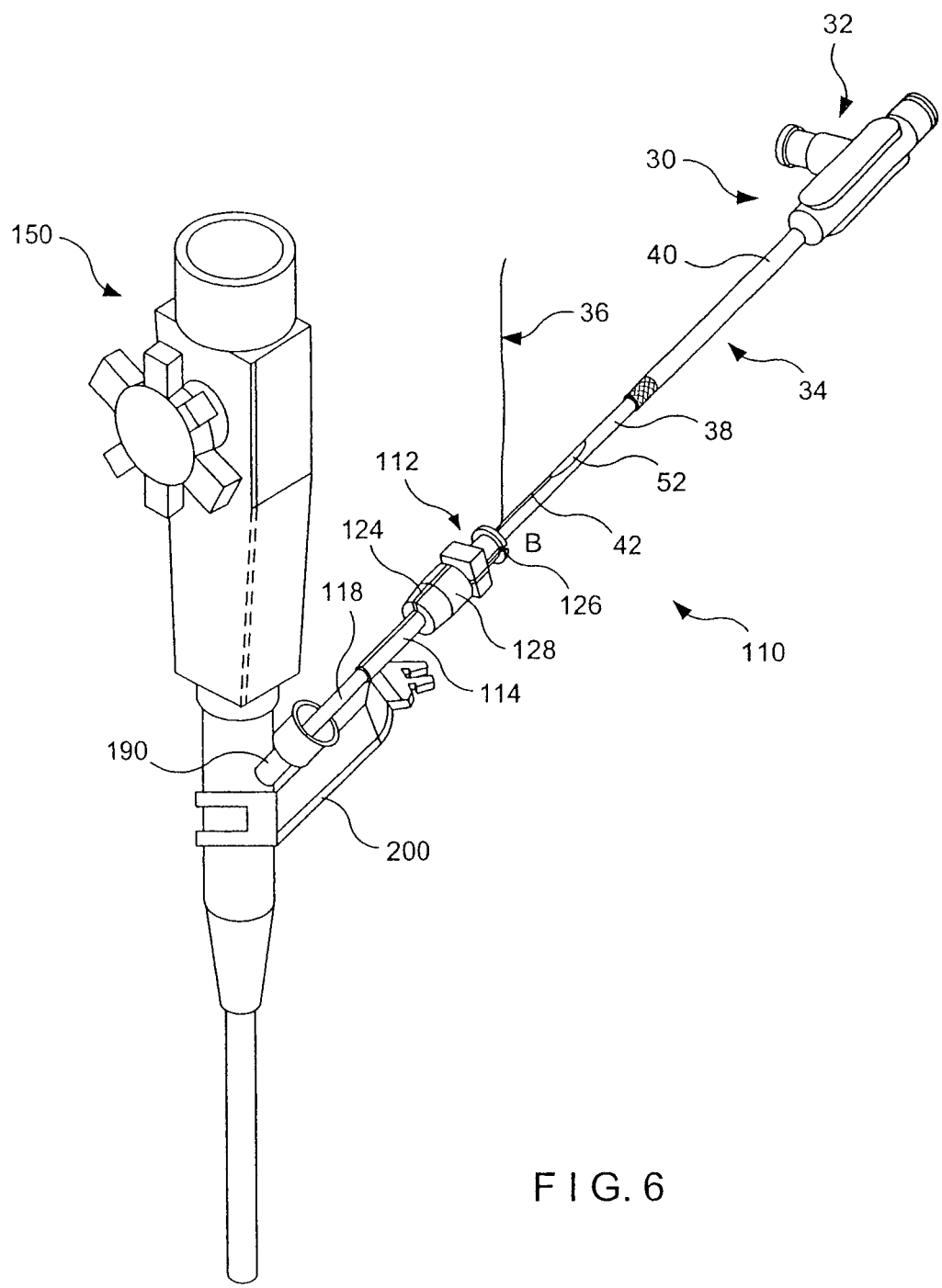
FIG. 6 is a perspective view showing a catheter assembly mounted on an endoscope, according to an embodiment of the present disclosure.
Figure 7A:
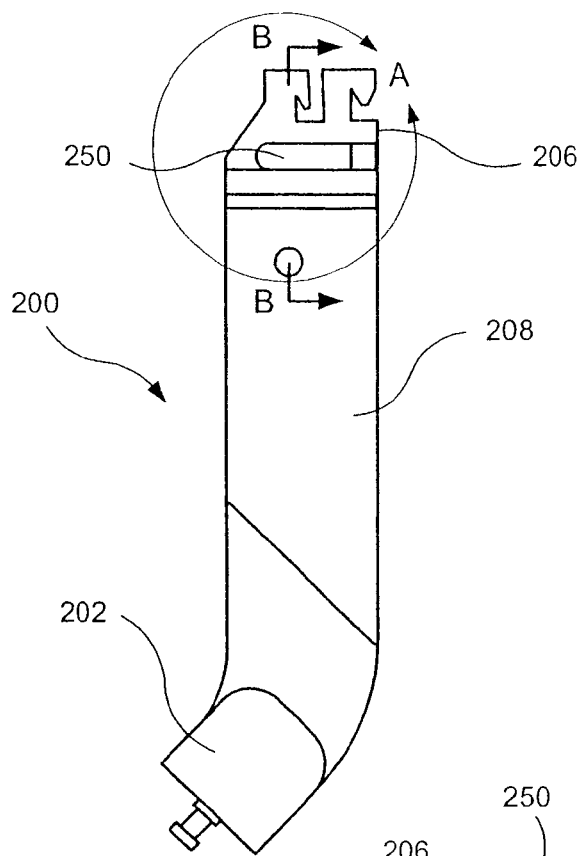
FIG. 7A shows a first side view of a guidewire locking arm according to an embodiment of the present disclosure.
Figure 7B:
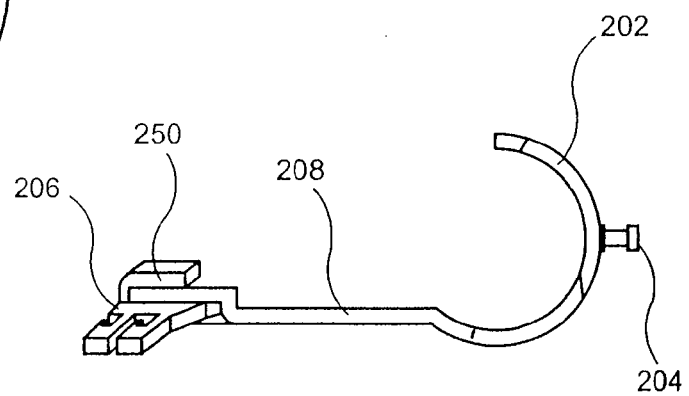
FIG. 7B shows a front view of the locking arm of FIG. 7A.
Figure 7C:
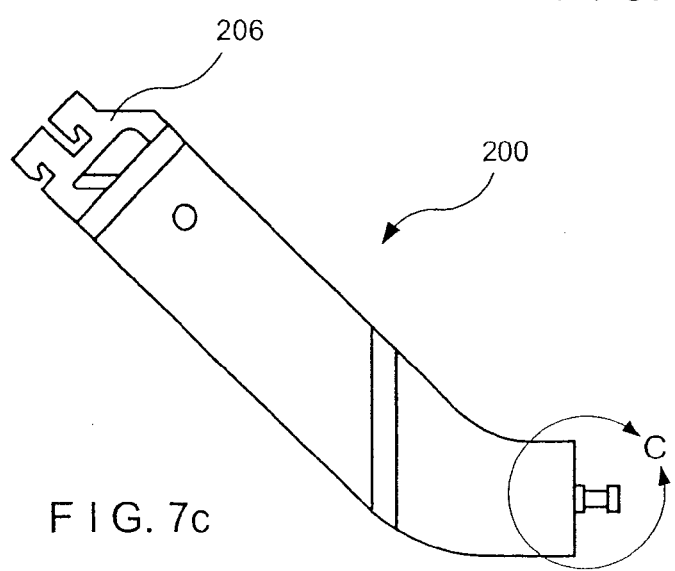
FIG. 7C shows a second side view of the locking arm of FIG. 7A.
Figure 8:
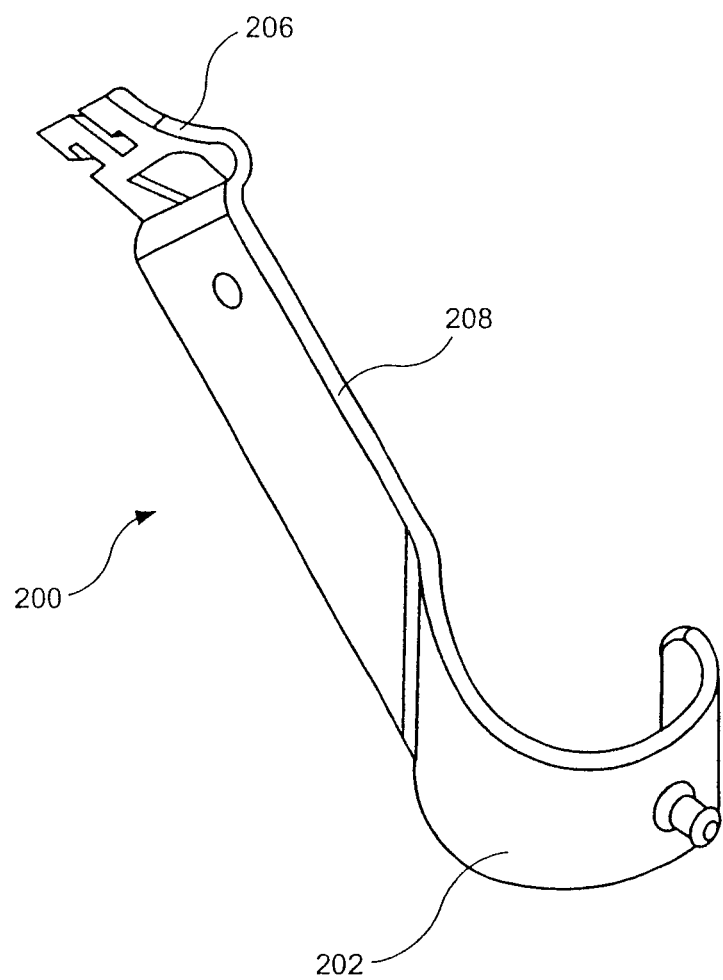
FIG. 8 is a perspective view of the locking arm shown in FIG. 7A.

FIG. 1 shows an exemplary embodiment of a catheter assembly 30 according to the present disclosure for use in accessing targeted anatomical regions through, e.g., the alimentary canal. The present disclosure incorporates features that allow rapid exchange of one or more catheters by a single operator. The catheter of the present disclosure allows shorter length guidewires to be used, resulting in procedures which require fewer medical personnel, are less time consuming, and less costly. Additionally, the present disclosure is adaptable to a variety of devices for catheter procedures within the alimentary canal or any other body lumen.

The catheter assembly 30 includes a catheter hub assembly 32 and a catheter 34 with a guidewire lumen 60 extending therethrough. As shown in FIGS. 2 and 3, a guidewire 36 may be inserted therein. The catheter 34 includes a shaft 38 which has a proximal end 40, a channel 42, a distal tip region 44, a distal end 46 and several internal lumens described in greater detail below. The catheter hub assembly 32 which is operably connected to a proximal end 40 of the shaft 38 may preferably be configured to couple to ancillary devices allowing access to one or more lumens within the shaft 38. In different embodiments, more than one guidewire lumen 60 may be provided in catheter assembly 30, to be used with additional guidewires.

The shaft 38 may preferably be a generally tubular member having a substantially uniform outer shape at the proximal end 40. As would be understood by those of skill in the art, the shaft 38 may be sized for slidable passage through the lumen of an endoscope or through a body lumen and may preferably be formed in an extrusion process of, e.g., a polymeric material. In one embodiment, the preferred polymeric material may be polytetrafluoroethylene, polyether block amide, nylon or a combination or blend of these. Catheters that are contemplated for used with the present disclosure include, but are not limited to, cannulas, sphincterotomes, cytology devices, and devices for stone retrieval and stent placement. The shaft 38 may further include a distal taper 48 tapering to the distal tip region 44. As would be understood by those skilled in the art, the distal tip region 44 may include high contrast, color-coded distal markers 50 and may be radiopaque for fluoroscopic visualization of the distal tip region 44 during catheter procedures.

The guidewire lumen 60 extends through the catheter 34 from a proximal end to a distal end thereof with a channel 42 forming a portion thereof extending between a channel proximal end 52 and a channel distal end 54. The channel 42 serves to contain, but not necessarily constrain, the guidewire 36 therein. The channel 42 allows radial removal of the guidewire 36 therefrom via a slot extending between the walls of the channel 42 and opening an interior of the guidewire lumen 60 to an outside of the catheter 34. As shown in FIG. 2, the channel 42 is substantially "U" shaped. However, the channel 42 may alternatively be shaped substantially like a letter "C" with sides of the channel extending inward from a maximum diameter to partially close the slot between the walls of the channel 42. The "C" shape of the channel may increase the overall strength of the shaft 38 to resist bending in the direction of the opening. This increased strength of the shaft 38 may then allow for greater force to be used in pushing the catheter 34 into the body.

In one embodiment, the channel 42 is sufficiently large to allow unhindered radial removal of the guidewire 36 from the channel 42 via the slot extending between the walls thereof. As shown in FIG. 2, the slot opening the channel 42 to an outside of the catheter 34 may be formed to be substantially equal in size to or slightly larger than a diameter of a guidewire to be used with the catheter 34, as described in greater detail below. This size selection allows deliberate removal of guidewire 36 from channel 42 while restraining the guidewire 36 from falling out of the guide lumen 60. Although it is recognized that the channel proximal end 52 may be located at any location distal of the proximal end 40 of the shaft 38, the channel distal end 54 is preferably located between 10 and 40 cm from the distal end 46 of the catheter shaft 38. The channel distal end 54 may more preferably be located between 20 and 30 cm and, most preferably, approximately 25 cm from the distal end 46.

As shown in FIGS. 1, 2 and 3, in a region proximal to the channel proximal end 52, the guidewire lumen 60 is completely sealed from an outside of the catheter 34. As described above and described more fully below, the portion of the guidewire lumen 60 between the channel proximal and distal ends 52, 54, respectively, (i.e., the channel 42) is open to the outside of the catheter 34 via a slot. The catheter 34 according to this exemplary embodiment also includes ancillary lumens 56 and 58 which may be used for a variety of medical purposes. As would be understood by those of skill in the art, the ancillary lumens 56 and 58 may preferably extend longitudinally between the proximal end 40 and the distal end 46 of the shaft 38 and may be used, for example, as injection lumens for high contrast media for visualization of a desired anatomical region. Additionally or alternatively, the ancillary lumens 56 and 58 may, for example, be used for or serve as part of another ancillary device, such as a cutting wire or a retrieval balloon, etc.

The guidewire lumen 60 preferably extends longitudinally between the proximal end 40 and the distal end 46 of the shaft 38, and is sized to receive the guidewire 36 slidably therein. In one example, the guidewire 36 has a diameter of between 0.6 mm and 0.9 mm. As would be understood, the guidewire lumen 60 may be formed integrally with the catheter shaft 38, as shown in FIG. 3 or, alternatively, may be formed as a separate tubular member coupled to the catheter shaft 38. In one preferred embodiment, the guidewire lumen 60 is a tubular member which is located proximate the distal end 46 of the shaft 38. However, the guidewire lumen 60 may be formed anywhere else along the shaft 38, may comprise an extension of the shaft 38 coupled to the distal end 46 thereof, or may run the entire length of the shaft 38, as would be understood by those skilled in the art.

In use, after a distal end of guidewire 36 has been positioned at a desired location within the body, the physician simply inserts a proximal end of the guidewire 36 into the guidewire lumen 60 via an opening at the distal end 46 of the catheter 34 and slides the catheter 34 distally along the guidewire 36. During the maneuver, the physician may grip the portion of the guidewire 36 extending distally of the distal end 46 of the catheter 34 to maintain the distal end of the guidewire 36 in the desired position within the body. When the proximal end of the guidewire 36 has reached the open channel 42, the proximal end of the guidewire is deflected out of the guidewire lumen 60 through the slot extending between the walls of the channel 42. The physician may then grasp the proximal end of the guidewire 36 and continue to slide the catheter 34 along the guidewire 36 until the distal end 46 of the catheter 34 reaches the desired location within the body. As the guidewire 36 is received within the guidewire lumen 60 only along a short portion of the length of the catheter 34, those skilled in the art will understand that the physician may at all times maintain his grasp on an exposed portion of the guidewire 36 to maintain it in position without the need for guidewire extenders, etc.

If during the procedure the catheter 34 is to be exchanged for another catheter as may be required when, for example, placing of multiple stents within a patient, the physician simply draws the catheter 34 proximally along the guidewire 36 while grasping the proximal end of the guidewire 36. When the distal end of the catheter 34 exits the body, the physician may then grasp the portion of the guidewire 36 extending distally of the catheter 34 and remove the catheter 34 completely from the guidewire 36. The loading process described above may then be repeated for the new catheter. Those skilled in the art will understand that the new catheter may be constructed as described above in regard to the catheter 34 or may be constructed in accord with any known catheter construction. The physician may also exchange the guidewire 36 while maintaining the catheter 34 in a desired position within the body, by performing the following steps. First, while grasping the proximal end of the catheter 34 to maintain the distal end 46 of the catheter 34 in the desired position within the body, the physician draws the guidewire 36 distally out of the guidewire lumen 60 and removes it from the body. Then, the new guidewire 36 is inserted into the guidewire lumen opening at the proximal end of the catheter 34 and is fed through the guidewire lumen 60, past the channel proximal end 52, through the channel 42 so that it passes into the portion of the guidewire lumen 60 extending distally of the channel distal end 54 and exits the distal end 46 of the catheter 34.

If catheter 34 later needs to be exchanged while maintaining the guidewire 36 in position, the physician grasps the proximal end of the guidewire 36 to maintain it in position and slides the catheter 34 proximally along the guidewire 36 until the channel proximal end 52 is located outside the body. The physician may then grasp the guidewire 36 from the channel 42 and draw the proximal end of the guidewire 36 distally through the proximal portion of the guidewire lumen 60, while holding the distal portion of the guidewire 36 stationary to maintain the position of the distal end of the guidewire 36. When the proximal end of the guidewire 36 has been removed from the guidewire lumen 60, the catheter 34 may be drawn proximally from the body with the guidewire 36 sliding out of the channel 42. When the distal end of the catheter 34 is outside the body, the physician grasps the portion of the guidewire 36 extending distally of the distal end 46 of the catheter 34 and withdraws the catheter 34 from the guidewire 36.

The endoscope and catheter according to the present disclosure may be used, for example, in the treatment of pathologies within a patient's biliary tree. Generally, for the treatment of pathologies within the patient's biliary tree an endoscopic biliary procedure is performed. During an endoscopic biliary procedure, the endoscope is introduced into the mouth of a patient and guided down the patient's alimentary canal through the esophagus, the stomach, and past the pyloric sphincter of the stomach into the duodenum. Once in the duodenum, the endoscope may be guided to a position in which its distal end is proximate to the target area (e.g., the papilla of vater). Throughout the procedure, the proximal end of the endoscope extends and remains outside the mouth of the patient, where it is accessible to the physician using the device.

FIG. 4A shows an exemplary embodiment according to the present disclosure of an endoscope sheath assembly 110. The endoscope exchange sheath assembly 110 may include a two-piece hub assembly 112, a sheath 114 and a defining lumen 116. The defining lumen 116 includes a slit 118 extending longitudinally over its length, terminating at a distal end 120 of the sheath assembly 110. The two-piece hub assembly 112 has a proximal hub portion 122 and a distal hub portion 124, axially rotatable relative to one another. The proximal hub portion 122 has a proximal slit 126 and the distal hub portion 124 has a distal slit 128. When the proximal hub portion 122 is in a position "A", as shown in FIG. 4A, the slit 118 is in alignment with the proximal and distal hub slits 126 and 128. This allows a guidewire to be radially slid into or out of the sheath assembly 110. In FIG. 4B the proximal hub portion 122 is shown in a position "B", rotated with respect to distal hub slit 128. In this position proximal slit 126 is out of alignment with distal slit 128, so that the guidewire cannot be removed. As would be understood by those of skill in the art, the proximal hub portion 122 may be set to position "B" when radial guidewire movement is not desired and returned to position "A" when removing the guidewire.

FIG. 5 shows an exemplary embodiment according to the present disclosure of a catheter assembly 30 as shown in FIG. 1, inserted through an endoscope sheath assembly 110 as shown in FIG. 4A. The catheter 34 is inserted through the sheath assembly 110, extending distally from the sheath distal end 120, with the guidewire 36 received within the guidewire lumen 60 and passing through the channel 42 thereof to the shaft distal end 46. The guidewire 36 passes through that portion of the catheter 34 which is received within and engaged by the hub assembly 112. In this embodiment, to perform a catheter exchange as described above, the physician must first rotate the proximal and distal hub portions, 122, 124, respectively, from the locked position "B" to the open position "A". Thereafter, the physician performs the same steps described above to perform the rapid exchange, except that the guidewire 36 must be drawn out of the slit 118 after it has been removed from the channel 42 so that the physician may grasp it.

Prior to positioning the endoscope within the patient, the catheter assembly 30 is fed onto the guidewire 36. Specifically, a distal end of the guidewire 36 is inserted into the guidewire lumen 60 via the channel distal end 54 and is passed therethrough to the catheter distal end 46. The guidewire 36 may be fed into the guidewire lumen 60 through channel 42 of catheter 34, and further to the distal end 46. From there, the guidewire 36 is advanced through the endoscope and extended from the distal end thereof to be advanced through the body lumen of the patient to the target area, e.g., using fluoroscopy to guide the guidewire. Once guidewire 36 has been positioned at the target area, the catheter assembly 30 is inserted into the endoscope and advanced therethrough along the guidewire 36 until the distal end 46 of the catheter 34 extends distally beyond the distal end of the endoscope. The catheter 34 is then further advanced distally along the guidewire 36 until the distal end 46 of the catheter 34 is in a desired position within the patient's body.

Once the distal end 46 of the catheter 34 has been positioned at the target area, medical procedures may be performed using the catheter 34. For example, contrast media such as radiopaque dye may be injected through the ancillary lumens 56 or 58 into the common bile duct for visualization of the duct. After the desired catheter procedure has been completed, the catheter assembly 30 may be exchanged or removed from the endoscope, leaving the guidewire 36 in position for other guidewire procedures to be carried out as described above.

Specifically, to remove the catheter 34 from the endoscope when using a catheter 34 according to the described exemplary embodiment, a proximal end of the guidewire 36 is grasped to prevent longitudinal movement thereof while the catheter 34 is retracted through the endoscope. Retraction of the catheter 34 while leaving the guidewire 36 in position within the patient is possible because the guidewire 36 is received within the catheter 34 for only the short distance between the channel distal end 54 and the catheter's distal end 46. Guidewire 36 is thus contained within the catheter 34 only along this short length, and a guidewire 36 double the length of the catheter 34 is not required to facilitate catheter exchanges. Thus a single operator may use one hand to grasp the portion of the guidewire 36 extending proximally from the catheter 34, while drawing the catheter 34 proximally from the body lumen with the other hand. When the distal end 46 of the catheter 34 is drawn out of the body, the operator may grasp the portion of the guidewire 36 extending distally of the distal end 46 of the catheter 34 and remove the catheter 34 completely from the guidewire 36. The accessible portion of the guidewire 36 is then held by the operator, while withdrawing the remaining portion of the catheter 34 completely over the guidewire 36. For example, this procedure may be carried out using a Rapid Exchange® catheter manufactured by Boston Scientific Corporation. According to embodiments of the present disclosure, the holding of the guidewire 36 is assisted by a guidewire locking device 200, which holds the guidewire 36 in place and frees the operator's hands for other tasks.

For example, if a stent (not shown) having an outside diameter larger than which can be accommodated by the sheath is to be advanced over the guidewire 36, the sheath assembly 110 may have to be exchanged. Alternatively, it may also be necessary to exchange both the sheath assembly 110 and the catheter assembly 30 simultaneously. In both cases a single operator is able to access a portion of the guidewire 36 between the distal end 46 of the catheter 34 and the proximal end of the endoscope 150, and to hold that portion of guidewire 36 in place while the catheter assembly 30 is completely removed or disengaged from the guidewire 36. As described below, a guidewire locking device 200 may be employed to lock in place a section of the guidewire 36, so that the operator is free to handle the stents, the catheter 34 and the sheath assembly 110 without displacing guidewire 36 from the target region in the patient's body.

FIGS. 7A-7C and 8 depict a guidewire locking device 200 according to the present disclosure. An attachment portion 202 is provided at one end of locking device 200, so that it may be securely connected to a medical tube such as endoscope 150. Attachment portion 202 may take different forms, as long as it provides a secure attachment to endoscope 150. For example, the exemplary embodiment shown includes an attachment portion 202 that is semicircular and is adapted to fit partially around the barrel of the endoscope 150. As will be understood by those skilled in the art, the diameter of the curved attachment portion 202 is selected to substantially match that of the endoscope 150 being used. Different versions of the locking device 200 may be provided, sized to fit different endoscopes as would be understood by those of skill in the art. Alternatively, the attachment portion 202 may be separate from the rest of the locking device 200, so that an appropriately sized attachment portion 202 may be used together with common components of the locking device 200 to assemble a locking device 200 adapted for a specific endoscope 150.

The attachment portion 202 may be designed to allow some relative movement of the locking device 200 with respect to the barrel of the endoscope 150. This permits the physician to finely adjust the position and orientation of the guidewire locking device 200 after it has been loosely mounted on the endoscope 150. As will be described below, the specific orientation of the locking device 200 relative to the access port 190 of the endoscope 150 is optimized to provide the best performance. After the locking device 200 has been placed in the correct orientation, it may be immobilized relative to the endoscope 150, for example, by tightening a strap around the endoscope barrel and securing it to a pin 204. In this manner, fine adjustment of the position of the locking device 200 may be obtained, which is then retained to prevent any further movement thereof. The locking device 200 may be attached to endoscope 150 either externally, as shown, or internally, and alternatively may be formed as an integral part of the endoscope 150.

Figure 9:
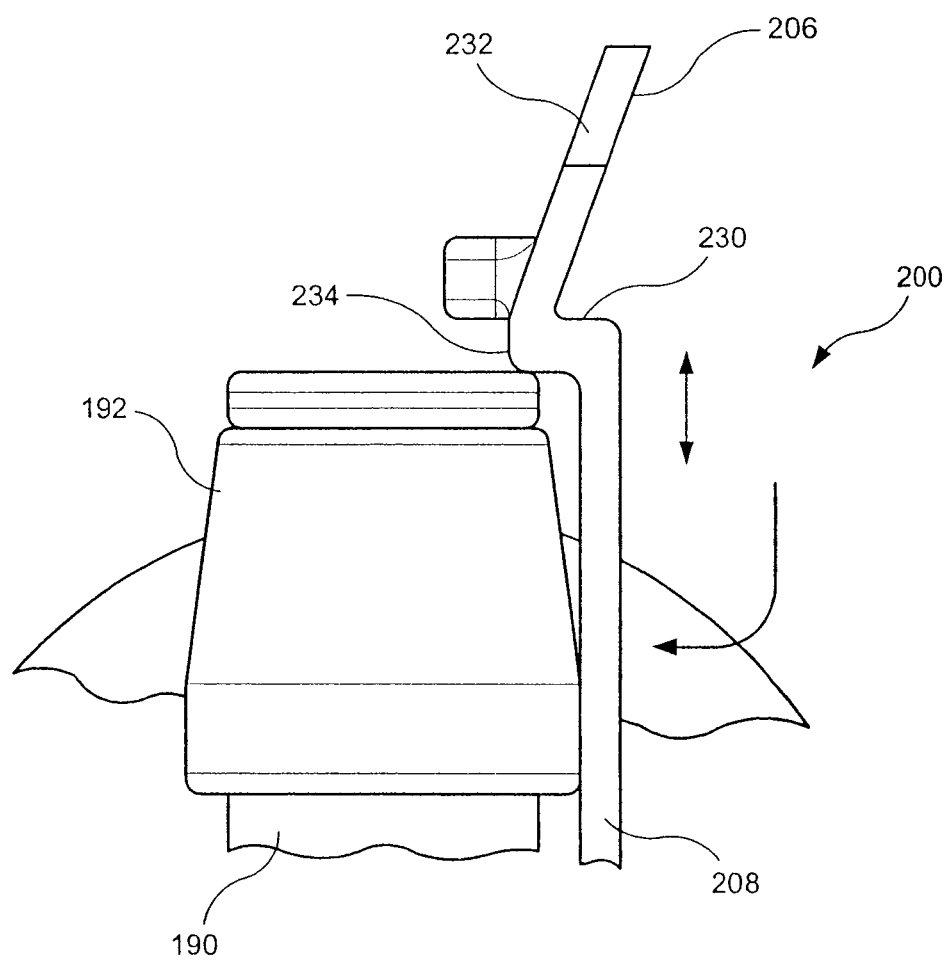
FIG. 9 is a fragmentary perspective view showing a detail of the locking arm mounted on the endoscope, according to the present disclosure.

Opposite of the attachment portion 202, the locking device 200 shown in FIGS. 7A-C and 8 includes an angled head 206 which is used to immobilize the guidewire 36 relative thereto. The angled head 206 may preferably be formed at the end of a substantially rigid body 208, which extends from the attachment portion 202. The rigid body 208 has a length and a shape that may vary according to the type of endoscope 150 used in the procedure. According to the disclosure, the rigid body 208 is shaped so as to place the angled head 206 in proximity to the opening of access port 190, substantially adjacent to the center of a biopsy channel of the endoscope 150. As shown in FIG. 9, the length of the body 208 is sufficient to reach the access port 190, and largely depends on the precise location where the attachment portion 202 connects to the endoscope 150, and on how far the access port 190 extends from the endoscope body. Accordingly, different designs of the rigid body 208 may be provided to fit different endoscopes. The locking device 200 may be made of metal or of polymeric materials which have sufficient stiffness to prevent unwanted movement of the angled head 206 during use. For example, thermoplastic polymers, thermoset polymers or other composites may be used to form the locking device 200. In one embodiment, a biopsy cap 192 is attached to the opening of the access port 190, to prevent contamination by foreign materials and to prevent spilling of bodily fluids from the port. In that case, the locking device 200 is sized to take into account the dimensions of the biopsy cap 192.

The angled head 206 includes many features designed to assist the physician in immobilizing elongated medical members, such as guidewires 36, which exit the endoscope 150 through the access port 190. In particular, multiple locking features 210 are formed on the angled head 206. In the exemplary embodiment shown, two locking features 210 are shown, each of which is capable of independently immobilizing a section of guidewire 36. It will be understood by those of skill in the art that additional locking features may be included, so that more than two guidewires may be locked in place. The number of locking features 210 actually present on a given locking device 200 may vary depending on the intended application, and on the amount of space available on the angled head 206. Alternatively, the locking features 210 may be designed to immobilize other types of elongated medical members. For example, a section of a catheter may be locked in place in the same manner, so that the physician can exchange a guidewire without displacing the catheter from its desired location. As described above, other elements used in endoscopic procedures may be exchanged in the same manner, such as, for example, the sheath assembly 110.

Figure 10:
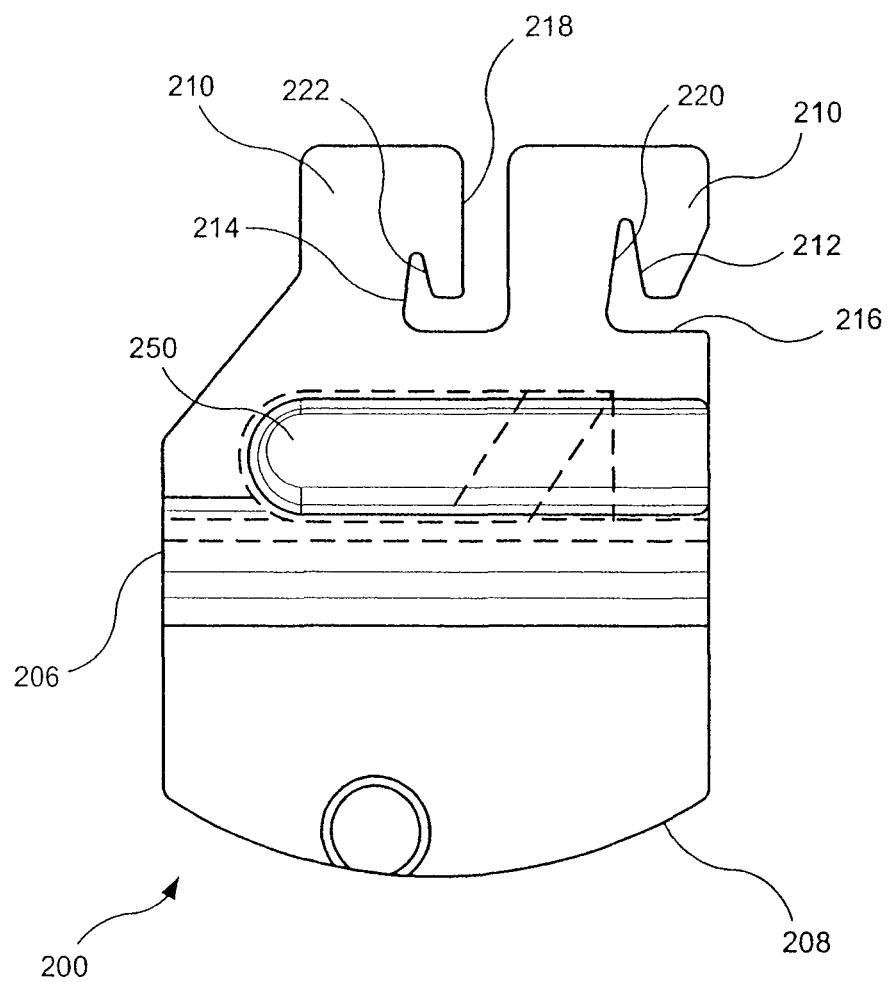
FIG. 10 is an enlarged detail view showing the locking features of the locking arm shown in FIGS. 7A and 8.

As shown in FIG. 10, the locking features 210 operate by frictionally maintaining a section of a guidewire 36 in place. For example, two J-shaped slots 212, 214 may be utilized for that purpose. Exemplary J-shaped slots 212, 214 are formed by entry slots 216, 218 and locking slots 220, 222. During use, a section of the guidewire 36 is inserted in the J-shaped slot 212 via the entry slot 216, and is then pushed by the physician into the locking slot 220 to be immobilized therein. In one example, the entry slot 216 is sufficiently large to allow free movement of the section of the guidewire 36, while the locking slot 220 is tapered to a size smaller than the section of the guidewire 36 to be immobilized, so that when the guidewire 36 is forced therein it is frictionally locked in place by the walls of the locking slot 220. An analogous process may be used to lock a second section of a guidewire 36 in the J-shaped slot 214. The purpose of the entry slots 212, 214 is to separate the multiple guidewires 36, so that each may be immobilized as well as released by the locking features 210 independently of the other. In this manner, the physician is given great flexibility in carrying out the procedure.

It will be apparent to those of skill in the art that other, different mechanisms may be employed to immobilize sections of the guidewire 36 in the locking features 210. For example, mechanical features that can bend, compress, twist, pinch or lock the guidewire 36 in place may be used. The J-shaped slots described above are simply one example of a simple, reliable mechanism to effectively lock a section of a guidewire 36 so that the physician's hands are freed to carry out other functions, such as exchanging a catheter associated with the guidewire 36. As shown in FIG. 10, the locking features 210 do not have to be identical, and each may be optimized to immobilize a specific size and type of elongated medical member. For example, the J-shaped slot 212 may be larger than the slot 214, to accommodate a larger guidewire 36 or catheter 34. Different types of locking features 210 may also be intermixed, for example a frictional element such as the J-shaped slot 212 may be combined with another type of mechanical locking feature, without departing from the scope of the present disclosure.

Figure 11:
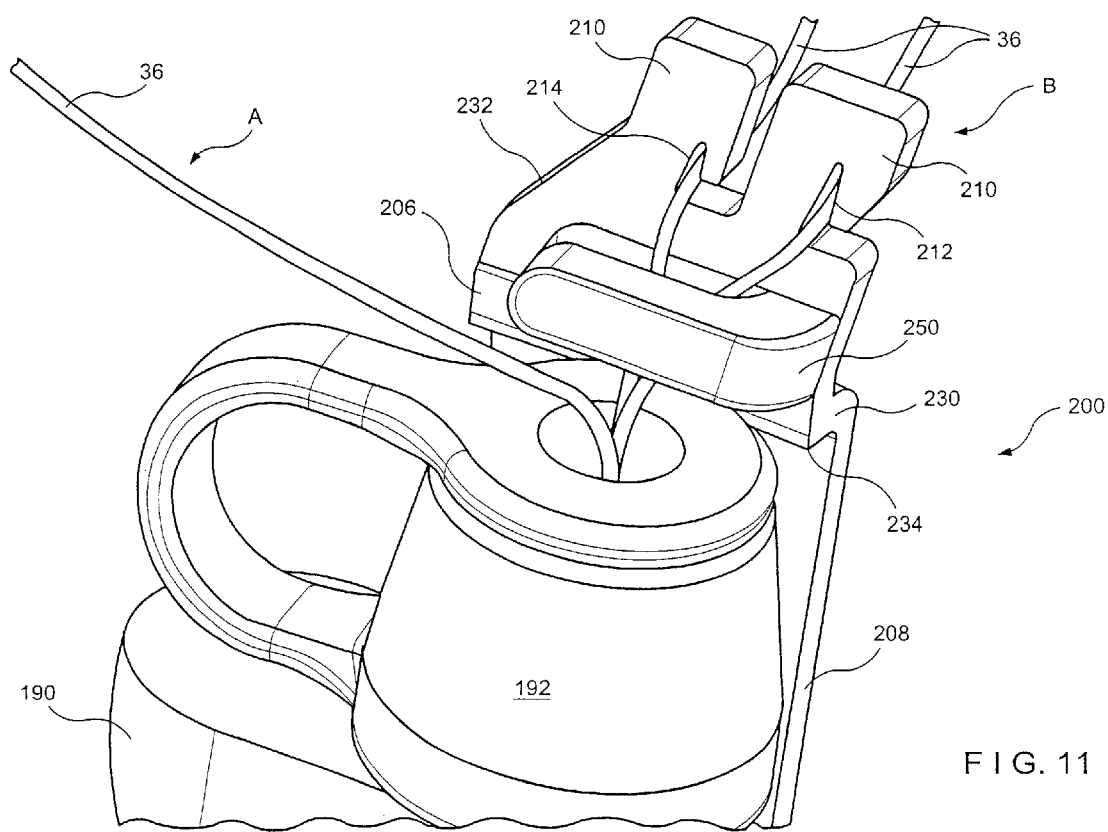
FIG. 11 is a side elevation view showing a detail of the locking arm mounted on the endoscope, according to the present disclosure.

The angled head 206 is designed to position the locking devices 210 formed thereon in a preferred orientation relative to the access port 190, and consequently relative to the guidewires 36 that exit the endoscope 150 therethrough. As can be seen in FIGS. 9 and 11, the angled head 206 has a first portion 230 that extends towards the opening of the access port 190. If a biopsy cap 192 is installed, this first portion 230 is designed to bring the locking features 210 substantially over the opening of the biopsy channel, so that guidewires 36 can be easily placed in contact with the locking features 210 without excessive manipulation. As discussed above, the specific size and orientation of the first portion 230 depends on the size and shape of the endoscope being used for the procedure. As shown in FIG. 9, the angled head 206 may also include an indexing protrusion 234, which is used to help obtain the correct alignment of the locking features 210 so that they overlie the access port 190. Since, in certain configurations, the locking device 200 may be longitudinally slidable over the endoscope 150 to let the physician fine tune its position, the indexing protrusion 234 may be designed to abut the biopsy cap 192 when the correct longitudinal position is reached.

The angled head 206 includes a second portion 232 that extends away from the opening of the access port 190, at a shallow angle in relation to a longitudinal axis of this opening. In the exemplary embodiment, the locking features 210 are formed on the second portion 232, whose orientation is selected to minimize the curvature of the guidewire(s) 36 as it extends from the access port 190 to the locking features 210. An additional consideration affecting selection of the angular orientation of the second portion 232 is to allow the physician to easily visualize the locking features 210 during the procedure. The more the angled head 206 diverges from the longitudinal axis, the easier it is for the physician to see the locking features 210. This is necessary so that the guidewires 36 can be easily inserted and immobilized in the locking features 210 without distracting the physician from other tasks. The angle at which the angled head 206 diverges from the longitudinal axis of the access port 190 is thus principally selected as a compromise to satisfy the two requirements of a large bending radius for guidewires 36, and of providing to the physician a good view of the locking devices 210. In addition, the angled head 206 is oriented so as not to interfere with the movement of the guidewires 36 when they are not locked in place.

In the exemplary embodiment, a locking arm 250 is provided that extends from the angled head 206. The locking arm 250 is used to further control the bending of the guidewires 36 as they extend from the access port 190 (or the biopsy cap 192) to the locking features 210. The locking arm 250, for example, extends parallel to the surface of the angled head 206, and forms a gap therewith. The guidewires 36 may be inserted in the gap defined by the locking arm 250, and then may be inserted into the locking features 210. The locking arm 250 keeps the guidewires 36 substantially parallel to the angled head 206, so that they do not bow excessively. Keeping the guidewires 36 substantially straight is beneficial, because that retains the greatest amount of column strength to the guidewire 36. If the guidewires 36 are allowed to bow excessively, their column strength is reduced, making them more susceptible to being displaced during the exchange procedure. Also, preventing the guidewire 36 from bowing facilitates the separation of the catheter 34 from the guidewire 36. As will be apparent to those of skill in the art, the locking arm 250 may extend from another portion of the locking device 200, and does not have to be an integral part of the angled head 206.

During an endoscopic operation, a guidewire 36 may, for example, exit the biopsy cap 192, and extend away from the endoscope 150 in an unrestrained position "A", as shown in FIG. 11, to be used to direct a catheter or other medical device to a desired location within a patient's body. As would be understood by those skilled in the art, two or more combinations of catheters and guidewires may be utilized with the same endoscope during a single procedure. If the physician desires to replace one or more catheters 34 without displacing the corresponding guidewire 36, the locking device 200 may be used to immobilize a portion of the guidewire 36, so that it will not be displaced as the catheter 34 is withdrawn and a new catheter 34 is introduced through the endoscope 150. Use of the locking device 200 frees the physician from having to manually hold the guidewire 36 in place while manipulating the old and new catheters. By moving the guidewire 36 into position "B", in engagement with the locking feature 210, the physician can easily exchange the catheter associated with that guidewire 36.

Once the locking device 200 is in position on the endoscope 150, the rigid body 208 of the locking device 200 is placed flush against the side of the access port 190, and the indexing protrusion 234 is moved to abut a top of the biopsy cap 192. The guidewire 36 may then be locked in place. The guidewire 36 is shown in the locked position "B", with a portion thereof held in the gap formed by the locking arm 250 and the surface of the angled head 206, and a section immobilized in the J-shaped slots 212, 214. The slots 212, 214 are aligned relative to the biopsy cap 192 so that the guidewires 36 do not bend excessively. The locking arm 250 further controls the position of the guidewires 36, to prevent them from bowing when they are inserted by the physician in the slots 212, 214. Due to the orientation of the angled head 206, the physician can easily see the slots 212, 214 while performing the procedure, and can easily move the guidewires 36 from the "free" position shown as position "A" to the "locked" position shown as position "B". As described above, the tapered shape of the locking arm 250 and the presence of multiple locking features 210 permit the physician to independently lock and release each of the guidewires 36, and to independently carry out the exchange of the catheters associated with each of those guidewires.

Figure 12:
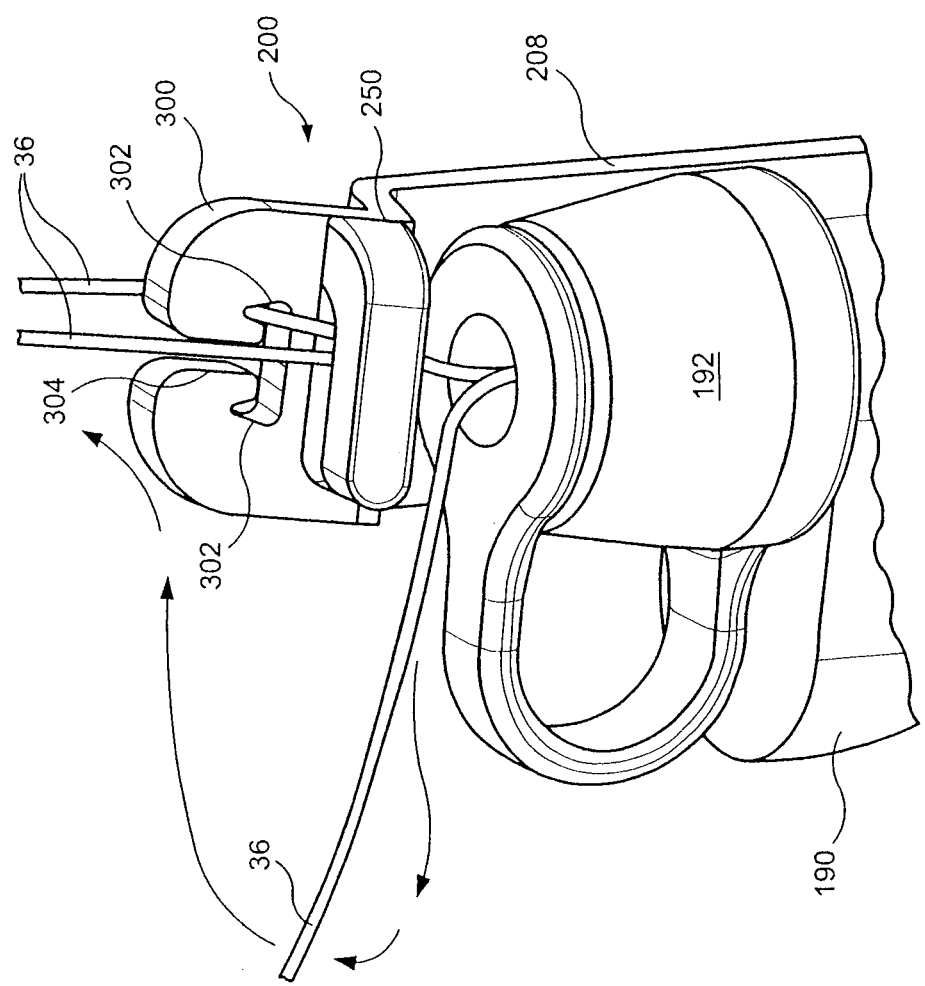
FIG. 12 is a fragmentary perspective view showing a different embodiment of the locking arm mounted on the endoscope, according to the present disclosure.

FIG. 12 shows a different exemplary embodiment of a locking device 200 according to the present disclosure. This embodiment includes an angled head 300 with two locking slots 302 that share a common entry slot 304. The position and orientation of the angled head 300 preferably conforms to the same considerations that were discussed with reference to FIGS. 9-11. However, the shape of the locking slots 302 is different. To lock the guidewires 36 in place, the physician inserts each of these guidewires 36 into the entry slot 304, and then further pushes each guidewire 36 into a corresponding one of the locking slots 302, to frictionally retain each guidewire 36 in place within a respective one of the locking slots 302. The locking arm 250 retains the same purpose of preventing excessive bowing of the guidewires 36, and of directing the guidewires 36 towards the locking slots 302 making the device easier to use.

The present disclosure has been described with reference to specific exemplary embodiments. Those skilled in the art will understand that changes may be made in the details of design of these embodiments, particularly in matters of shape, size, material and the arrangement of the various parts. For example, additional locking features may be provided, and different types of endoscopes and catheters useful in varied procedures may be used. Accordingly, various modifications and changes may be made to the embodiments without departing from the broadest scope of the disclosure as set forth in the claims that follow. The specifications and drawings are, therefore, to be regarded in an illustrative rather than a restrictive sense.

What is claimed is:

1. A locking device for use with an endoscope, the locking device comprising:
   a curved associating portion for associating the locking device with an endoscope;
   wherein the curved associating portion includes a pin;
   a strap coupled to the pin, the strap being configured to wrap around the endoscope;
   a middle portion extending from the curved associating portion;
   an angled head extending at an angle relative to the middle portion;
   a first lock disposed at the angled head;
   a second lock disposed at the angled head and positioned adjacent to the first lock;
   a locking arm disposed at the angled head;
   wherein the locking arm is capable of overlying an access port of the endoscope;
   wherein the locking device includes an abutting portion for abutting a top surface of a biopsy cap attached to the access port, the abutting portion being disposed between the middle portion and the angled head; and
   wherein the locking arm is longitudinally spaced apart from the abutting portion.

2. The locking device of claim 1, wherein the curved associating portion is disposed at an angle relative to the middle portion.

3. The locking device of claim 1, wherein the curved associating portion forms a C-shaped curve.

4. The locking device of claim 1, wherein the middle portion is substantially planar.

5. The locking device of claim 1, wherein the middle portion is rectangular in shape.

6. The locking device of claim 1, wherein the first lock is a J-shaped opening formed in the angled head.

7. The locking device of claim 1, wherein the first lock and the second lock are disposed in a side-by-side arrangement.

8. The locking device of claim 1, wherein the locking arm is disposed closer to the middle portion than the first lock, the second lock, or both.

9. The locking device of claim 1, wherein the locking arm is configured to overlie an opening formed in a biopsy cap.

10. The locking device of claim 1, wherein the abutting portion is disposed at a substantially right angle relative to the middle portion.

11. The locking device of claim 1, wherein the abutting portion is configured to abut a top surface of a biopsy cap.

\* \* \* \* \*

UNITED STATES PATENT AND TRADEMARK OFFICE
CERTIFICATE OF CORRECTION

| | | |
|---|---|---|
| PATENT NO. | : 8,647,256 B2 | Page 1 of 1 |
| APPLICATION NO. | : 12/891066 | |
| DATED | : February 11, 2014 | |
| INVENTOR(S) | : Oscar Carrillo, Jr. | |

It is certified that error appears in the above-identified patent and that said Letters Patent is hereby corrected as shown below:

In the Specification

Column 2
Line 67: after "FIG. 1 taken along line", insert -- III-III; --.

Signed and Sealed this
Tenth Day of June, 2014

Michelle K. Lee
*Deputy Director of the United States Patent and Trademark Office*